United States Patent [19]

Wurtman

[11] 4,296,119
[45] Oct. 20, 1981

[54] PROCESS AND COMPOSITION FOR REDUCING BLOOD PRESSURE IN ANIMALS

[75] Inventor: Richard J. Wurtman, Waban, Mass.

[73] Assignee: Massachusetts Institute of Technology, Cambridge, Mass.

[21] Appl. No.: 963,857

[22] Filed: Nov. 27, 1978

Related U.S. Application Data

[63] Continuation-in-part of Ser. No. 898,740, Apr. 24, 1978, abandoned.

[51] Int. Cl.$^3$ ............................................. A61K 31/40
[52] U.S. Cl. .................................................. 424/274
[58] Field of Search ................................ 424/319, 274

[56] References Cited

U.S. PATENT DOCUMENTS 3,360,434  12/1967  Udenfriend et al. ................. 424/319
3,362,879  1/1968   Udenfriend et al. ................. 424/319

OTHER PUBLICATIONS

Chem. Abst., 82—25836h (1975).
Chem. Abst., 85—91734m (1976).

Primary Examiner—Stanley J. Friedman
Attorney, Agent, or Firm—Arthur A. Smith, Jr.; Paul J. Cook

[57] ABSTRACT

Blood pressure in animals is reduced by administering tyrosine, a tyrosine precursor, tryptophan or mixtures thereof, either alone or in combination with a substance which is known to reduce blood pressure. A novel composition is provided comprising a unit dosage form of tyrosine, a precursor for tyrosine, tryptophan or mixtures thereof and a substance which is known to reduce blood pressure.

2 Claims, 1 Drawing Figure

PROCESS AND COMPOSITION FOR REDUCING BLOOD PRESSURE IN ANIMALS

The Government has rights in this invention pursuant to Grant No. AM-14228 awarded by the National Institute of Health.

REFERENCE TO RELATED APPLICATION

This application is a continuation-in-part of application Ser. No. 898,740, filed Apr. 24, 1978 now abandoned.

BACKGROUND OF THE INVENTION

This invention relates to a method and composition for reducing blood pressure in animals.

This invention relates to a method and composition for reducing blood pressure in animals by regulating (increasing and decreasing) the levels of dopamine and norepinephrine in neuronal synapses.

It is well known that the neurotransmitters dopamine and norepinephrine are derived from dihydroxyphenylalanine (DOPA). DOPA is, in turn, produced in neurons by the enzymatic hydroxylation of the amino acid tyrosine. This process is catalyzed by the enzyme tyrosine hydroxylase. The DOPA is decarboxylated to dopamine by the enzyme aromatic L-amino acid decarboxylase (AAAD) and norepinephrine is produced from dopamine in neurons that also contain the enzyme dopamine beta-hydroxylase. It is also known that within this reaction chain, the rate-limiting step is the conversion of tyrosine to DOPA. For this reason, DOPA has been administered to patients who suffer medical disability resulting from dopamine deficiency in diseases such as Parkinson's Disease. Unfortunately, DOPA, when administered, is taken up by cells throughout the body and converted to dopamine and this interferes with the normal metabolic processes in these other cells. In addition, DOPA interferes with the body's normal storage of the neurotransmitter serotonin, and lowers brain levels of the compound S-adenosylmethionine. It is believed that these effects contribute to such unwanted side-effects as the "On-Off Phenomenon" and, in some patients, psychotic symptoms. Other types of drugs that act by increasing dopamine and norepinephrine levels in synapses include the Monoamine Oxidase Inhibitors (which slow the destruction of these neurotransmitters) and the tricyclic antidepressants; these compounds, which are used in treating diseases like depression are also relatively non-specific—producing many chemical effects besides increasing synaptic dopamine and norepinephrine levels—and thus have a range of unwanted side-effects such as the dangerous increases in blood pressure that occur when people receiving monoamine oxidase inhibitors eat certain foods.

The transmission of signals across dopaminergic and noradrenergic synapses can also be enhanced by giving drugs that act directly to activate post-synaptic dopamine and norepinephrine receptors; these include apomorphine and bromocryptine (dopamine receptors) and clonidine and alpha-methyldopa (Aldomet—which is converted in the brain to alpha-methylnorepinephrine) (norepinephrine receptors). Like the other drugs listed above, these compounds act on their respective receptors throughout the brain and the rest of the body, thus causing unwanted side-effects.

Other diseases appear to be caused by the presence of excessive quantities of dopamine or norepinephrine within synapses including psychosis (too much dopamine), movement disorders like tardive dyskinesia and the Gilles de la Tourette Syndrome (too much dopamine), and hypertension and cardiac arrhythmias (too much norepinephrine released from sympathetic neurons). These diseases now usually are treated by drugs that block the interactions of dopamine or norepinephrine with their post-synaptic receptors, such as phenothiazines or butyrophenones. However, these agents all exhibit some non-specific actions as well, and thus cause side-effects.

Prior attempts to increase or decrease the levels of dopamine or norepinephrine by modifying neuronal tyrosine levels had been deemed unsuccessful because the total amounts of these compounds in brains and tissues were not noted to change. It was first observed in Wurtman et al (Science 185:183–184, July 12, 1974) that increases in brain DOPA concentrations, which, under the conditions of the experiments, varied in proportion to the rates at which dopamine and norepinephrine were being synthesized, could be obtained by increasing brain tyrosine concentrations, and that decreases in brain DOPA concentrations could be produced by giving rats treatments that decreased brain tyrosine. An example of a treatment that increased brain tyrosine was the administration of tyrosine itself; an example of a treatment that decreased brain tyrosine was the administration of one of the other neutral amino acids, e.g., leucine, that competes with tyrosine in the plasma for uptake into the brain. Prior to that disclosure, it had been believed that the rate-limitng enzyme, tyrosine hydroxylase, was so saturated with tyrosine, that increases or decreases in brain tyrosine levels would not affect tyrosine's conversion to DOPA. In neither the above Wurtman et al article nor a subsequent paper by Gibson and Wurtman (Biochem. Parmacology, 26:1137–1142, June 1977) was it actually shown that such changes in DOPA accumulation were accompanied by changes in brain dopamine nor norepinephrine levels. Furthermore, in neither was it shown that changing brain tyrosine levels had any effect on the amounts of dopamine nor norepinephrine released into synapses.

It would be highly desirable to provide a means for increasing or decreasing the amounts of dopamine and/or norepinephrine that actually are present within synapses. Such changes in synaptic transmitter levels need not be associated with changes in the total amounts of dopamine or norepinephrine present in the brain or other tissues, inasmuch as it is now well known that not all of the molecules of the transmitters that are stored in neurons are equally accessable for release into synapses. Furthermore, it would be desirable to provide such a means which is biochemically specific and which lacks the undesirable side-effects associated with administration of DOPA, the MAO inhibitors, the phenothiazines, and the other drugs described above. Such a means might by itself be therapeutic in various disease states. Alternatively, it could be used in combination with drugs to amplify their therapeutic effects.

At the present time, some of the most widely used medicaments for lowering blood pressure such as $\alpha$-methyl dopa (Aldomet), 11,17$\alpha$-dimethoxy-18$\beta$-[(3,4,5-trimethoxybenzoyl)oxy]-3$\beta$, 20$\alpha$-yohimban-16$\beta$-carboxylic acid methyl ester (Reserpine) or 2-(2,6-dichlorophenylamino) 2-imidazoline hydrochloride (Clonidine hydrochloride) also stimulate the secretion of prolactin in humans. This side-effect is potentially objectionable, inasmuch as in recent years, it has been reported that high circulating levels of prolactin can accelerate the growth of some breast cancers and, in males, can cause impotence. Accordingly, it would be highly desirable to provide a means for reducing hypertension, which could serve either as a substitute for or an adjunct to present means, and which would not enhance prolactin secretion.

SUMMARY OF THE INVENTION

The present invention provides a method of composition for treating hypertension which is associated with a relative deficiency of norepinephrine in synapses of the central nervous system. This invention is based upon the discovery that treatments that increase or decrease neuronal tyrosine levels can also cause corresponding increases or reductions in the amounts of norepinephrine released into synapses. The tyrosine, or a tyrosine precursor such as phenylalanine, or other neutral amino acids can be administered alone or in admixtures, with or without drugs, in order to raise or lower brain tyrosine (and phenylalanine) levels, and thereby to treat hypertension associated with deficiency of norepinphrine in central nervous system synapses. By varying the proportion of typtophan, another amino acid, in the mixture, or by giving tryptophan without other amino acids, the synthesis and synaptic release of serotonin, another brain neurotransmitter, can similarly be controlled. Increases in serotonin synthesis can also reduce blood pressure. The use of tryptophan to increase serotonin synthesis is preferable to the use of another amino acid, 5-hydroxytryptophan, which is not present in foods nor normally consumed, inasmuch as the tryptophan is converted to serotonin only within neurons that normally make this transmitter, while the 5-hydroxytryptophan can be converted to serotonin non-specifically, in many types of cells, and can thus produce numerous side-effects. Increased synaptic norepinephrine levels are obtained by giving tyrosine regardless of whether the norepinephrine-releasing neurons are or are not especially active. Decreases or increases in serotonin release can be obtained by lowering or raising brain tryptophan levels. By regulating the proportion of tyrosine in a given mixture of neutral amino acids, it can be caused to increase or decrease norepinephrine release. Phenylalanine can, in low doses, be used in place of tyrosine. Tryptophan's porportion in the neutral amino acid mixture can be used to regulate serotonin's release into synapses while regulating norepinephrine release as described herein. The amino acids can be administered intraperitonally, subcutaneously, intramuscularly or orally; in the form of free amino acids, salts, esters, peptides, or compounds which are converted to the amino acids in the body (e.g., alpha-keto acids).

DETAILED DESCRIPTION OF SPECIFIC EMBODIMENTS

Figure 1:
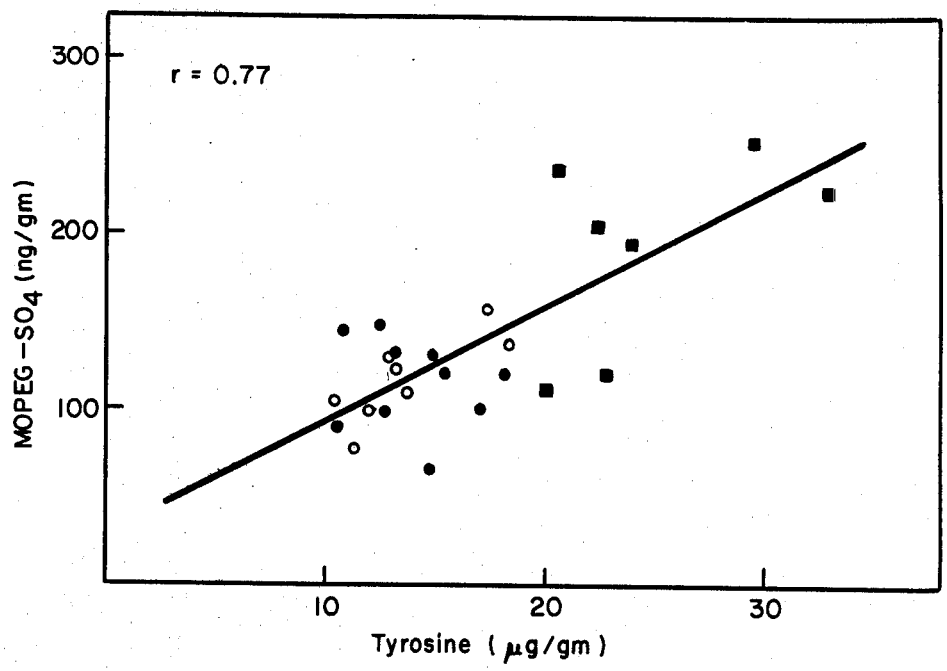

In accordance with this invention, tyrosine and/or a tyrosine precursor such as phenylalanine and/or other neutral amino acids is administered to a patient either alone or in combination with one or more drugs known to reduce blood pressure, thereby to increase the level of norepinephrine which is released into synapses. Serotonin release also can be controlled at the same time by giving tryptophan alone or varying its proportion in the amino acid mixture. Release of norepinephrine or serotonin into synapses can be varied using amino acid mixtures whether or not the norepinephrine-releasing or serotonin-releasing neutrons are especially active. Similarly, decreases in norepinephrine or serotonin release can be produced by administering mixtures of amino acids that compete with tyrosine or tyrptophan levels for uptake into the brain, thereby decreasing brain tyrosine or tryptophan levels in order, for example, to treat patients afflicted with low blood pressure of central nervous system origin.

While the exact mechanism by which tyrosine produces reduced blood pressure has not yet been determined, it is believed that the sum of tyrosine's efforts on the organism differs from those of Adlomet, Clonidine hydrochloride or Reserpine since tyrosine does not increase prolactin secretion.

The administration of the compositions employed in the present invention can be effected orally, intraperitonally, subcutaneously, intraveneously or intramuscularly; the amino acids can be used as such, as salts or esters, as peptides or as compounds which are metabolized to give the amino acids in vivo (e.g., Alpha-keto amino acids). They can also be given with or without a carbohydrate which, by eliciting insulin serotonin, modifies the brain uptakes. Conveniently, the compositions employed in this invention are admixed or dissolved in any innocuous vehicle such as water or sterile saline solution or in tablet or powder form containing the usual solid diluents or carriers. When producing a lowering of blood pressure, the compositions employed in the present invention are administered in concentrations to avoid undesirable side-effects. The compound, tyrosine, is employed in dosages sufficient to effect lowering of blood pressure while minimizing the possibility of producing undesirable side-effects such as orthostatic hypotension. In humans, useful dosages are between about 10 mg/kg and 200 mg/kg, preferably between about 25 mg/kg and 100 mg/kg body weight. Dosages below about 5 mg/kg body weight do not produce significant lowering of blood pressure while concentrations above about 200 mg/kg body weight do not produce significant additional lowering of blood pressure and may produce undesirable side-effects. When utilizing this invention, lowering of blood pressure is produced for about 4–24 hours per administration.

In another aspect of this invention, it has been found that the co-administration of tyrosine with such anti-hypertensive drugs as the thiazide duiretics, e.g. hydrochlorothiazide, reserpine, α-methyl dopa, hydralazine, guanethidine, phenoxybenzamine, clonidine, propranolol, furosemide, ethacrynic acid, or spironolactone, or their pharmaceutically acceptable salts (which dissociate in vivo to produce one of these compounds) produces an additive effect of lowering blood pressure. In order to obtain this additive effect, useful concentrations of tyrosine are between about 5 and 100 mg/kg body weight compounder with the main anti-hypertension agent. In these compositions, Reserpine is employed in amounts between 0.007 and 0.0035 mg/kg, hydrochlorothazide in amounts between about 0.25 mg/kg and 2 mg/kg and Clonidine in amounts between about 0.0014 mg/kg and 0.035 mg/kg. In some situations, phenylalanine can be used as a substitute for tyrosine in as much of this amino acid is converted to tyrosine in the liver, and released into the blood stream for uptake into the brain. However, plasma phenylalanine levels should be less than about double those of tyrosine, since at the higher levels, phenylalanine competes with tyrosine for uptake into the brain, and can inhibit the enzyme tyrosine hydroxylase. The anti-hypentensive effects of the amino acids can also be potentiated by using them with carbidopa, low doses of benzaseride, or other peripherally-acting decarboxylase inhibitors.

When there is need to sustain or increase brain serotonin levels while increasing dopamine or norepinephrine release, these compositions also contain tryptophan in addition to tyrosine and/or phenylalanine and other neutral amino acids. This combination is especially useful in treating certain types of depression, or sleep disorders. Tryptophan, alone or with an insulin-releasing carbohydrate, but without other amino acids, can also be used to lower blood pressure. Other neutral amino acids than those compositions can include the branched-chain amino acids (leucine, isoleucine, valine), as well as methionine, threonine and histidine. The amino acids can be supplied as monomers, as salts or esters, or as compounds converted to them in the body. They can also be given as constituents of foods.

The following examples illustrate the present invention and are not intended to limit the same.

EXAMPLE I

This example illustrates that brain norepinephrine can be synthesized by increasing brain tyrosine levels.

This example shows that the rate at which 3-methoxy-4-hydroxy-phenylethyleneglycol-sulfate (MOPEG-$SO_4$), the major brain metabolite of norepinephrine, accumulates in rat brain also varies as a function of brain tyrosine levels. This shows that brain tyrosine levels affect not only the synthesis, but also the turnover and release of brain norepinephrine.

Male Sprague-Dawley rats (Charles River Breeding Laboratories, Wilmington, MA) weighing 150 g were housed in hanging cages (6-8 per cage), given ad libitum access to tap water and a 26% protein diet (Charles River Rat-Mouse-Hamster Maintenance Formula 24RF), and maintained under light (300 microwatts/$cm^2$; Vita-Lite, Duro-Test Corp., North Bergen, N.J.) between 8 AM and 8 PM daily. Rats used for diet experiments were fasted overnight and then allowed to consume the experimental diet starting at 10 AM. Diets of different composition were prepared in agar gel (35 g/100 ml of water) as described by Gibson et al, Biochem. Pharmacol., 26, 1137-1142 (1977). All amino acids and drugs were injected intraperitoneally.

Norepinephrine synthesis and turnover in brain neurons were estimated by measuring the rate of accumulation of MOPEG-$SO_4$ after probenecid administration or exposure to a cold environment. The MOPEG-$SO_4$ in brain homogenates was isolated using an anion exchanges column (A-25 DEAE Sephadex; Pharmacia, Piscataway, N.J.); the method used was basically that of Meek and Neff; Br. J. Pharmacol., 45, 435-441 (1972), but modified to allow both tyrosine and MOPEG-$SO_4$ to be measured in the same sample. An aliquot of each homogenate (in 0.15 M $ZnSO_4$) was first assayed for tyrosine by the method of Waalkes and Udenfriend, J. Lab. Clin. Med., 50, 733-736 (1957). An equal volume of 0.15 M barium hydroxide was then added to the remaining homogenate, which was rehomogenized (Polytron, Brinkman Instruments, N.Y.), centrifuged and assayed for MOPEG-$SO_4$ by the method of Meek and Neff above. Recoveries of MOPEG-$SO_4$ and tyrosine from whole brain homogenates were 70-75% and 85-95%, respectively.

Tyrosine (Grand Island Biological Co., Long Island, N.Y.) and probenecid (Sigma Chemical Co., St. Louis, MO), which are poorly soluble in water, were dissolved in dilute NaOH; the solutions were then buffered to pH 7.4 with hydrochloric acid and brought to a known volume with saline. This yielded a fine suspension that was suitable for injection.

In experiments on stress produced by exposure to cold, animals received the more soluble ethyl-ester form of tyrosine (J. T. Baker, Phillipsburg, N.J.), instead of tyrosine itself, to raise brain tyrosine levels. Data were analyzed by one-way or two-way analysis of variance.

Probenecid treatment significantly raised the MOPEG-$SO_4$ level in brain from 123 ng/g in diluent-injected controls to 175 ng/g in probenecid-treated animals ($P<0.001$) (Table I). Tyrosine administration alone had no effect on brain MOPEG-$SO_4$; however, pretreatment with this amino acid significantly enhanced the probenecid-induced rise in MOPEG-$SO_4$ (to 203 ng/g, as compared with 175 ng/kg in rats receiving probenecid alone ($P<0.01$) (Table I).

TABLE I

Accumulation of MOPEG—$SO_4$ after Probenecid Administration and Pretreatment with Tryosine

| Pretreatment | Brain Tyrosine Level ($\mu g/g$) | | Brain MOPEG—$SO_4$ Level (ng/g) | |
| --- | --- | --- | --- | --- |
| | Diluent | Probenecid | Diluent | Probenecid |
| Diluent | 13.9 ± 0.5 | 15.7 ± | 123 ± 6 | 175 ± 6 |
| Tyrosine | 23.3 ± 1.5 | 24.7 ± | 127 ± 2 | 203 ± 8 |

Note: In each of 3 experiments, groups of 4-6 rats were injected with either a dose of tyrosine (100 mg/kg, i.p.) known to accelerate brain dopa synthesis or its diluent and, 30 min. later, with probenecid (400 mg/kg, i.p.) or its diluent. Animals were killed 60 min. after the second injection, and their whole brains were analyzed for tryosine and MOPEG-$SO_4$. Tryosine administration significantly raised brain tryosine levels ($P<0.001$), whereas probenecid failed to modify brain tyrosine or its response to exogenous tyrosine. Probenecid significantly raised brain MOPEG-$SO_4$ ($P<0.001$), and tyrosine pretreatment significantly enhanced this response ($P<0.01$). Data were analyzed by two-way analysis of variance. Values are expressed as means±SEM.

Placing the rats in a cold environment (4° C.) increases norepinephrine turnover; this accelerates the formation of both norepinephrine itself and its metabolite, MOPEG-$SO_4$, in brain neurons. The rats were exposed to cold to determine whether treatments that changed brain tyrosine levels could influence the rate at which the brain accumulated MOPEG-$SO_4$ in rats exposed to cold stress and not given probenecid (FIG. 1).

Exposure to cold for 1 hr. increased brain MOPEG-$SO_4$ levels by about 40% (from 80 ng/g to 114 ng/g; $P<0.01$). In animals treated with either of the amino acids or with saline, brain tyrosine levels paralleled, and were significantly correlated with, those of MOPEG-$SO_4$ ($r=77$, $P<0.05$; FIG. 1). Pretreatment with tyrosine raised brain tyrosine levels by about 80% (from 13.3 $\mu g/g$, in saline-injected animals, to 24.6 $\mu g/g$; $P<0.01$) and those of MOPEG-$SO_4$ by 70% (from 114 mg/g to 193 ng/g; $P<0.01$). Pretreatment with Valine failed, in this study, to cause significant alterations in brain tyrosine of MOPEG-$SO_4$ levels (14.3 $\mu g/g$ and 117 ng/g respectively); however, brain tyrosine and MOPEG-$SO_4$ levels were also significantly correlated in these animals, as in other experimental groups (FIG. 1).

The relationship shown in FIG. 1 was obtained as follows: Groups of rats were injected intraperitoneally with Valine (200 mg/kg), an amino acid that competes with tyrosine for uptake into the brain (8), or with tyrosine 125 mg/kg of the ethyl ester) or saline; 30 min. later they were placed in single cages in a cold (4° C.) environment. After 1 hr., all animals were killed, and their whole brains were injected with saline and left at room temperature (22° C.), also in single cages, for 90 min. Each point represents the tyrosine and MOPEG-SO$_4$ levels present in a single brain. Data were pooled from several experiments. Brain tyrosine and MOPEG-SO$_4$ levels in animals kept at room temperature were 14.6 μg/g and 80 ng/g, respectively. In FIG. 1, the symbols are as follows: closed circles, animals pretreated with Valine; open circles, animals pretreated with saline; closed squares, animals pretreated with tyrosine.

To determine whether physiological variations in brain tyrosine level might also influence brain norepinephrine synthesis and turnover (as estimated by measuring MOPEG-SO$_4$ levels), the accumulation of this metabolite in animals exposed to a cold environment was examined after being allowed to consume a single meal that would be likely to elevate tyrosine levels.

Animals that had been fasted overnight were given access to either a protein-free (0% casein) or a 40% casein meal between 10 and 11 AM; they were then placed in the cold (4° C.) for 1 hr., after which they were killed, and their brains analyzed for tyrosine and MOPEG-SO$_4$. Fasted control animals remained at room temperature (22° C.) during this 2-hr. period.

Exposure to cold accelerated the accumulation of MOPEG-SO$_4$ in brains of fasted rats, from 123 ng/g (in fasted control animals kept at 22° C.) to 163 ng/g ($P<0.05$); this treatment had no effect on brain tyrosine levels (10.0 μg/g vs. 10.5 μg/g). Among animals placed in the cold, consumption of either a 0% or a 40% casein meal enhanced brain MOPEG-SO$_4$ accumulation by 40–50% (Table II; $P<0.-1$). The 0% casein meal increased brain tyrosin by about 40% ($P<0.01$), whereas the 40% casein meal increased brain tyrosin by 77% ($P<0.01$).

When the consumption of a protein-free meal failed to elevate brain tryosin levels, brain MOPEG-SO$_4$ levels also failed to rise (Table II). Among protein-fed animals in this study, the brain tyrosine level increased by about 50% (from 13.4 to 19.5 μg/g, $P<0.01$), and brain MOPEG-SO$_4$ rose in parallel.

These data show that treatments that increased brain tyrosine levels can accelerate the accumulation of the norepinephrine metabolite MOPEG-SO$_4$ in the brains of rats pretreated with probenecid or exposed to a cold environment. Such treatments can be pharmacologic (i.e., intraperitoneal injection of tyrosine) or physiologic (i.e., consumption of a high-protein meal). They are compatible with the high Km of tyrosine hydroxylase for its substrate, relative to brain tyrosine concentrations. The enzyme is especially vulnerable to substrate limitation when it has been activated, inasmuch as activation selectively enhances its affinity for its cofactor.

MOPEG-SO$_4$ is the major metabolite of norepinephrine formed in rat brain and it is transported out of the brain by a probenecid-sensitive mechanism. After probenecid administration, MOPEG-SO$_4$ accumulates at a linear rate in rat brain for at least 60 min. Since brain norepinephrine levels remain constant during this interval, the rate of MOPEG-SO$_4$ accumulation provided a useful index of the rate of norepinephrine synthesis. This rate apparently is lower in unstressed, probenecid-treated rats than in animals placed in the cold (Tables I and II); however, in both circumstances, it is dependent on brain tyrosine levels.

TABLE II

Brain MOPEG—SO$_4$ Accumulation after Ingestion of a Single Protein-free or 40% Protein Diet among Rats Placed in a Cold Environment

| Treatment | Tyrosine (g/g) | MOPEG—SO$_4$ (ng/g) |
|---|---|---|
| EXPERIMENT I | | |
| Fasted | 10.5 ± 0.55 | 163 ± 9 |
| Protein-free (0% Casein) | 14.4 ± 0.24* | 239 ± 17 |
| 40% Casein | 18.1 ± 0.85*+ | 228 ± 9* |
| EXPERIMENT II | | |
| Fasted | 13.4 ± 0.67 | 195 ± 9 |
| Protein-free (0% Casein) | 13.3 ± 0.81 | 182 ± 18 |
| 40% Casein | 19.5 ± 1.03* | 264 ± 20* |

*Values are significantly different from corresponding fasted group ($P < 0.01$).
+Values are significantly different from corresponding protein-free group ($P < 0.01$).

Note: Groups of 4–6 rats were fasted overnight and then allowed access to one of the test diets at 10 AM. At 11 AM, animals were placed in an environmental chamber at 4° C. for 1 hr. They were killed at noon, and their whole brains were analyzed for tyrosine and MOPEG-SO$_4$. Animals given protein-free and 40% protein diets consumed 9.7 and 10.5 g, respectively, in Experiment I, and 6.2 and 8.0 g in Experiment II. Data presented as means±SEM.

EXAMPLE II

This example illustrates that tyrosine produces a lowering of blood pressure in animals.

Male spontaneously hypertensive (SH) rats of the Okamoto strain weighing between 280 and 320 grams and having resting blood pressures between 180–200 mm Hg were used in these experiments. Blood pressure was estimated by the indirect tail cuff method using a Narco Bio-systems pneumatic pulse transducer. The rats were warmed for 20 min. at 37° C. just prior to each measurement and 8 blood pressure readings were taken and averaged for each rat at each time-point. In the dose-response experiment (Table 2), groups of three rats were injected i.p. with each of the indicated doses of tyrosine methylester immediately after their baseline blood pressures had been determined. Their blood pressures were remeasured 1.5 hours later and the results are expressed as change from baseline. In the Tyrosine-Valine experiment (Table 3), groups of 3 rats received the indicated treatments immediately after their baseline blood pressures had been established. At hourly intervals thereafter, blood pressures were remeasured and expressed as changes from baseline.

Tyrosine administration (as its more soluble, hydrated methyl ester) caused a dose-related and highly significant reduction in blood pressure (Table 2). Maximum reductions occurred when the dose was 200–400 mg/kg (equal to 156–312 mg/kg of pure tyrosine). The administration of Valine, another neutral amino acid, failed to modify blood pressure (Table 3), but this dose (100 mg/kg almost completely blocked the hypotensive action of an equal dose of tyrosine (given, in this experiment, as the pure amino acid).

These data show that tyrosine, given in doses that have been shown to increase brain norepinephrine (Example I), causes the anticipated reduction in blood pressure among hypertensive animals. In other studies, it was found that the administration of tyrosine (100 mg/kg) to normotensive rats can also cause a slight decline in blood pressure, however, far less than the decline seen in hypertension.

TABLE 2

Dose-Response Cure for tyrosine methylester and Blood Pressure

| Dose (mg/kg) | Fall in Blood Pressure (mm Hg) |
| --- | --- |
| 0 (vehicle) | 2 ± 2 |
| 25 | 1 ± 4 |
| 50 | 11 ± 6 |
| 100 | 25 ± 4 |
| 200 | 40 ± 5 |
| 400 | 42 ± 3 |

TABLE 3

Effects of Tyrosine (free base) and Valine on Blood Pressure

| | Fall in Blood Pressure (mm Hg) | |
| --- | --- | --- |
| Treatment | 1 hour | 2 hours |
| Vehicle (2 mg/kg) | −2 ± 2 | 2 ± 2 |
| Valine (100 mg/kg) | 0 ± 2 | 0 ± 2 |
| Tyrosine (100 mg/kg) | 40 ± 7 | 41 ± 7 |
| Tyrosine plus Valine (100 mg/kg each) | 8 ± 4 | 8 ± 2 |

EXAMPLE III

This example illustrates that tryptophan produces a lowering of blood pressure in hypertensive animals.

The animals, basic experimental conditions, and blood pressure-measuring techniques were the same as those described in EXAMPLE II. Groups of 4 SH rats received an injection of L-tryptophan (free base), and blood pressures were measured at various intervals thereafter. As indicated in Table IV, a dose of 125 mg/kg caused a 42 mm Hg drop in blood pressure within 3 hrs. of tryptophan injection. This effect was blocked by coadministration of known serotonin receptor-antagonist (metergoline 2 mg/kg), indicating that the tryptophan-induced reduction in blood pressure probably resulted from increases in serotonin synthesis within and release from, brain neurons normally utilizing this transmitter.

TABLE VI

Tryptophan-Induced Reduction in Blood Pressure of Spontaneously Hypertensive Rats.

| | Time (minute) | |
| --- | --- | --- |
| Treatment | 90 | 150 |
| | (mm hg) | |
| Vehicle | −3 ± 3 | −4 ± 2 |
| Tryptophan | −25 ± 4 | −42 ± 6 |
| Metergoline | −14 ± 3 | −15 ± 3 |
| Tryptophan + Metergoline | −22 ± 9 | −11 ± 2 |

Groups of 4 rats received vehicle or tryptophan (125 mg/kg,ip), and blood pressures were measured 90 or 180 min. later. Metergoline (2mg/kg,ip) was injected 20 minutes prior to vehicle or tryptophan. Data are presented as the *change* in blood pressure compared to values obtained at 0-time, just before animals were injected, and are given as means±standard errors. The reduction in blood pressure seen 90 and 180 min. after tryptophan injection was statistically significant, compared to vehicle (P<0.05). Pretreatment with metergoline, a serotonin receptor blocker, clearly antagonized the blood-pressure lowering effect of L-tryptophan (at 180 minutes).

I claim:

1. The process for reducing blood pressure in an animal afflicted with high blood pressure which comprises administering to said animal tryptophan to the animal in an amount effective to reduce blood pressure of at least about 5 mg/kg body weight.

2. The process of claim 1 wherein the animal is a human.

* * * * *